United States Patent

Graves et al.

[11] Patent Number: 6,159,422
[45] Date of Patent: *Dec. 12, 2000

[54] METHODS AND APPARATUS FOR THE TREATMENT OF HAZARDOUS BIOLOGICAL WASTE MATERIALS

[75] Inventors: Clinton G. Graves; Clinton G. Graves, II, both of Danville, Calif.

[73] Assignee: Graves' Trust Group, Danville, Calif.

[*] Notice: This patent is subject to a terminal disclaimer.

[21] Appl. No.: 09/196,565

[22] Filed: Nov. 20, 1998

Related U.S. Application Data

[63] Continuation-in-part of application No. 08/769,494, Dec. 18, 1996, Pat. No. 5,920,799, which is a continuation-in-part of application No. 08/365,666, Dec. 29, 1994, Pat. No. 5,633,424.

[51] Int. Cl.[7] .......................................... A61L 2/00
[52] U.S. Cl. ................. 422/22; 422/23; 422/33; 422/4; 422/121; 422/186; 422/305; 388/227
[58] Field of Search ................. 422/22, 23, 33, 422/186, 295, 305, 306, 906, 121, 4; 588/227

[56] References Cited

U.S. PATENT DOCUMENTS

| | | | |
|---|---|---|---|
| 4,207,286 | 6/1980 | Boucher | 422/21 |
| 4,699,689 | 10/1987 | Bersin | 156/643 |
| 4,902,631 | 2/1990 | Downey et al. | 437/7 |
| 4,976,920 | 12/1990 | Jacob | 422/23 |
| 5,115,166 | 5/1992 | Campbell et al. | 315/111.21 |
| 5,171,525 | 12/1992 | Jacob | 422/23 |
| 5,184,046 | 2/1993 | Campbell | 315/111.21 |
| 5,200,158 | 4/1993 | Jacob | 422/292 |
| 5,213,758 | 5/1993 | Kawashima et al. | 422/21 |
| 5,223,231 | 6/1993 | Drake | 422/297 |
| 5,325,020 | 6/1994 | Campbell et al. | 315/111.21 |
| 5,633,424 | 5/1997 | Graves et al. | 588/227 |
| 5,920,799 | 7/1999 | Graves et al. | 438/798 |

FOREIGN PATENT DOCUMENTS

| | | |
|---|---|---|
| 0 387 022 A2 | 9/1990 | European Pat. Off. . |
| 2 274 947 | 8/1994 | United Kingdom . |
| WO 93/12821 | 7/1993 | WIPO . |
| WO 96/21473 | 7/1996 | WIPO . |

*Primary Examiner*—Krisanne Thornton
*Attorney, Agent, or Firm*—Townsend and Townsend and Crew LLP

[57] ABSTRACT

The invention provides methods and apparatus for treating hazardous biological wastes. According to one exemplary method, a biological waste material is placed into a chamber and a vacuum is applied to the chamber. After the pressure within the chamber is sufficiently reduced, water vapor is introduced into the chamber and electromagnetic radiation energy is applied to produce a plasma. In one particularly preferable aspect, the chamber is allowed to reach a static condition before the water vapor is introduced. In this way, the water vapor is able to equally distribute itself throughout the volume of the chamber so that an equally distributed plasma can be produced upon application of the electromagnetic radiation energy.

34 Claims, 6 Drawing Sheets

METHODS AND APPARATUS FOR THE TREATMENT OF HAZARDOUS BIOLOGICAL WASTE MATERIALS

CROSS REFERENCE TO RELATED APPLICATIONS

This application is a continuation in part application of U.S. patent application Ser. No. 08/769,494, filed Dec. 18, 1996, now U.S. Pat. No. 5,920,799 which is a continuation in part of U.S. patent application Ser. No. 08/365,666, filed Dec. 29, 1994 (now U.S. Pat. No. 5,633,424), the complete disclosures of which are herein incorporated by reference.

BACKGROUND OF THE INVENTION

1. Field of the Invention

This invention relates generally to methods and apparatus for sterilizing articles and hazardous biological waste, and for the treatment of various substrates. In particular, the invention provides methods and apparatus for sterilizing articles and biological waste with a gas plasma generated from a gas mixture of oxidizing and reducing agents. Methods and apparatus are also provided for treating, e.g. stripping, cleaning, plasma treating, etching or depositing a film, various substrates with a plasma having a generally uniform density. In one particular aspect, this invention provides for the sterilization of articles and biological waste with a gas plasma generated from water vapor.

A variety of sterilization methods have been proposed for sterilizing a wide range of articles such as medical products, surgical instruments, pharmaceutical products, and the like. One common method is by subjecting the articles to a gas such as ethylene oxide or other disinfecting gases. Irradiation procedures have also been proposed for sterilizing articles such as medical products.

One expectation for all sterilizing procedures is that they must effectively kill all organisms without damage to the articles or goods being sterilized. Although some sterilization procedures meet these criteria, including the use of ethylene oxide and other procedures, many sterilizers using such gases suffer from number of serious drawbacks. For example, use of such gases is often too corrosive for the articles being sterilized or their packaging materials. Another drawback is that a toxic residue usually remains on the sterilized articles. In another drawback that affects all traditional methods of sterilization, although the microorganisms are usually destroyed by the plasma, the destroyed microorganisms still physically remain on the articles.

Sterilization gas procedures and irradiation procedures often expose workers and the environment to unacceptable safety standards. Such exposure is becoming increasingly more undesirable, particularly in light of state and federal legislation restricting the use of hazardous materials.

Such restrictions are forcing hospitals and other medical facilities to search for other alternatives. One such alternative is a plasma sterilizer. Plasma sterilizers operate by injecting a gas into a chamber and applying electromagnetic radiation energy to the gas in the chamber which in turn ionizes the body of gas. The ionized gas should be highly reactive and reacts with microorganisms on the surface of the articles to be sterilized. The reactions between the ionized gas and the microorganisms should effectively destroy the microorganisms. Sterilizing plasmas have been generated with a wide variety of gases as set forth generally in U.S. Pat. No. 5,184,046, the disclosure of which is herein incorporated by reference.

One drawback with using such plasma sterilizers is that it is often difficult to ensure that all of the articles in the sterilizer have been completely sterilized. Such a problem arises because of the difficulty in achieving uniform gas dynamics and uniform plasma density when the articles being sterilized are of different sizes or shapes. This problem is compounded by the use of non-cylindrical reaction chambers and differing batch sizes. The non-uniformity of the gas dynamics results in a non-uniform plasma density, which in turn provides a non-uniform plasma treatment and insufficient sterilization.

Another problem experienced in sterilizing articles is the problem of maintaining the sterility of the articles during packaging. Current sterilization techniques, such as plasma sterilization and gas sterilization, generally require the articles to be sterilized and then subsequently packaged. To maintain sterility during packaging, the articles are packaged in a sterile environment. Such a procedure is inconvenient and expensive.

The treatment of hazardous biological waste is also of interest to the invention. Hazardous biological waste is typically collected at the point of source and is usually consolidated with other hazardous biological waste from other sources and different locations. The handling, transportation, and storage of these materials can be problematic and can require special training, handling and tracking. Furthermore, there is a high risk of accidental contamination associated with the handling and storage of such wastes.

To destroy such wastes, the wastes are usually placed in an incinerator and burned at about 3000 degrees C. The burning of the hazardous biological waste in this manner poses various problems since many of the packaging materials are constructed from plastics and release toxic gases when burned.

The treatment of various substrates, such as semiconductor and microelectronic substrates, has also proved to be difficult and challenging. Traditionally, such substrates were processed using wet chemistries. Since the substrates were relatively small and the line geometries were relatively large, non-uniformity of the chemical treatment was not generally problematic. With the demand for larger sized substrates, most manufacturers have resorted to the use of gas plasma processes. However, due to the relatively large size of the substrates, e.g. 400 mm by 400 mm or larger, such processes have proved to be generally ineffective. For example, the achievement of uniform gas dynamics and uniform plasma density within relatively large reaction chambers has been difficult, if not impossible. As a result, both substrate sizes and batch sizes have remained small. Further, such processes have generally produced low yields.

It would therefore be desirable to provide methods and apparatus to overcome or reduce such problems relating to plasma sterilization, the treatment of hazardous biological waste, and the treatment of various substrates. In particular, the methods and apparatus should provide for plasma sterilization that is not corrosive to the articles and does not leave toxic residues on the articles. The methods and apparatus should not only be able to effectively destroy the microorganisms, but also to remove them from the articles. Further, the methods and apparatus should provide for uniform plasma distribution, thereby insuring uniform sterilization regardless of the chamber geometry or the size and geometry of the articles to be sterilized. It would further be desirable to provide methods and apparatus for sterilizing articles within packaging suitable for delivery to an end user.

In the case of biological wastes, it would be desirable to treat the hazardous waste (including gasses surrounding the waste) at the production site so that no special handling, transportation or storage of the waste will be required.

2. Description of the Background Art

U.S. Pat. Nos. 5,115,166, 5,184,046, and 5,325,020 describe various apparatus and methods for plasma sterilization.

U.S. Pat. No. 4,207,286 describes a sterilization method using a continuous flow, low pressure gas plasma.

SUMMARY OF THE INVENTION

The invention provides methods and apparatus for sterilizing articles, for sterilizing hazardous biological waste, and for treating various substrates using a gas plasma. To accommodate the treatment of biological waste, the invention provides various improvements to the systems and methods described in copending U.S. patent application Ser. No. 08/769,494, filed Dec. 18, 1996, and U.S. Pat. No. 5,633,424, the complete disclosures of which are herein incorporated by reference.

According to one particular sterilization method, an article or an amount of biological waste is placed into a sterilization chamber and a vacuum is applied to the chamber to reduce the pressure within the chamber. With the pressure reduced, water vapor is introduced into the chamber. The water vapor can be introduced alone or can optionally be introduced with a carrier gas. With the water vapor in the chamber, an electromagnetic radiation energy is applied to the chamber to produce a plasma. The electromagnetic radiation energy excites the water molecules and causes them to disassociate thereby creating reactive radicals. The reactive radicals vaporize and combine with the by-products of the spores and other microorganisms and to effectively destroy and remove the spores and other microorganisms from the articles or waste, thereby sterilizing the articles or waste.

In an exemplary aspect, the carrier gas comprises air. Alternatively, the carrier gas can be a gas selected from the group consisting of argon, hydrogen, oxygen, nitrogen, helium, nitrogen tri-fluoride, and nitrous oxide. The electromagnetic radiation energy applied to the chamber is preferably in the range from about 5 KHz to 10 GHz, and more preferably at about 2.45 GHz. Such a wavelength is preferable because of its effectiveness in disassociating the hydrogen and oxygen atoms of the water vapor.

When the water vapor is introduced into the chamber, the pressure within the chamber is preferably within the range from about 10 mTorr to 10 Torr. In another aspect, the temperature within the chamber is preferably in the range from about 25° C. to 300° C.

In an alternative method for sterilizing articles or biological waste, at least one article (or an amount of waste) is placed into a sterilization chamber and a vacuum is applied to the chamber until a predetermined pressure is reached within the chamber. Once such a pressure is reached, application of the vacuum is ceased and a static condition is allowed to develop within the chamber. Once a static condition has been reached, an amount of gas is introduced into the chamber and is allowed to uniformly distribute throughout the chamber. Because of the static condition within the chamber, pressure is equal throughout the chamber allowing the concentration of the gas to readily become uniform throughout the entire volume of the chamber. In such a state, electromagnetic radiation energy is applied to the chamber to produce a plasma.

After the plasma has had sufficient time to react with the spores and other microorganisms, the electromagnetic radiation power is ceased and any gases are exhausted from the chamber. One or more cycles can be applied. In a preferable aspect, the gas introduced into the chamber is water vapor. When water vapor is used to produce the plasma, the reactions within the chamber produce water vapor, oxygen, and nitrogen with small amounts of carbon dioxide and carbon monoxide. Such gases can be safely exhausted into the atmosphere.

After the gases are exhausted into the atmosphere, the cycle of applying a vacuum to the chamber, allowing a static condition to develop, introducing the gas into the chamber, and applying electromagnetic radiation energy are again repeated as necessary to ensure that the articles or waste within the chamber are sufficiently sterilized.

The invention provides an apparatus that may be used to sterilize articles or hazardous biological waste, or to treat various substrates. The apparatus includes a treatment chamber and both a vacuum pump and a gas source in communication with the chamber. The vacuum pump allows the pressure within the chamber to be reduced. Once the pressure is reduced, the gas source can be employed to introduce a gas into the chamber. The apparatus further includes an electromagnetic radiation energy source to produce a plasma from the gas within the chamber. A controller is provided for cyclically actuating the vacuum pump, the gas source, and the electromagnetic radiation energy source. In a preferable aspect, the controller is configured so that the vacuum pump, the gas source, and the electromagnetic radiation energy source are actuated at separate times. In this way, the apparatus can be operated in a cyclical manner to continuously produce and exhaust a plasma. Operation in this manner allows articles or waste to be uniformly sterilized and allows for uniform treatment of substrates.

In particular, the controller allows the vacuum pump to reduce the pressure in the chamber to a desired pressure. At this point, the controller stops the application of vacuum and allows the chamber to reach a static condition. When such a condition is reached, the controller actuates the gas source to inject an amount of gas into the chamber. Since the chamber is in a static condition, the gas equally distributes throughout the chamber. At this point, the electromagnetic radiation energy source is actuated by the controller to produce a uniformly distributed plasma within the chamber to uniformly sterilize the articles or waste or to treat the substrates. After reaction of the plasma with the microorganisms on the articles or waste, the resulting gases are exhausted and the controller sends a signal to repeat the cycle as often as is desired.

In a preferable aspect, the vacuum pump is connected to the chamber by a tube, and the controller includes a rotatable disk having an orifice that can be aligned with the tube as the disk is rotated. In this manner, each time the orifice comes in alignment with the tube, a vacuum is created within the chamber. The rotating disk also serves as a timer to actuate the injection of the gas and the application of the electromagnetic radiation energy. A sensor is preferably employed to sense the degree of rotation of the disk so that a signal can be sent to actuate the gas source or the electromagnetic radiation energy source at the appropriate times. In this way, the cycle of the apparatus is controlled by the rotation of the disk.

The invention further provides an exemplary method for treating a hazardous biological waste. According to the method, the waste is initially placed into a chamber that is employed to sterilize the waste. A reactor is coupled to the chamber and a vacuum is applied to the reactor to reduce the pressure within the reactor. An amount of starting gas, i.e. a gas which will produce a gas plasma when subjected to electromagnetic radiation (such as water vapor), is introduced into the reactor and electromagnetic radiation is applied to the starting gas in the reactor to produce a plasma within the reactor. Once the plasma has been created in the reactor, contaminated waste gas from the chamber is transferred into the reactor. In this way, hazardous gases which surround the waste (which is placed into the chamber) is transferred to the reactor where it is sterilized before being exhausted into the atmosphere.

Upon transfer of the waste gas from the chamber to the reactor, the pressure within the chamber is reduced. When the pressure within the chamber has reached a desired level, an amount of starting gas is introduced into the chamber and electromagnetic radiation energy is applied to the starting gas in the chamber to produce a plasma within the chamber in a manner similar to that previously described. In this way, the waste within the chamber is also sterilized.

In one particular aspect, the contaminated waste gas is transferred to the reactor due to the vacuum condition within the reactor (which is in communication with the chamber). In this way, the vacuum is used to reduce the pressure within the reactor so that a plasma may be produced within the reactor, to transfer waste gasses from the chamber to the reactor, and to reduce the pressure within the chamber so that a plasma may be produced within the chamber. Preferably, a metering valve is disposed between the chamber and the reactor to control the amount of waste gas that is introduced into the reactor. This in turn provides a way to insure that excessive waste gas is not transferred to the reactor before it can be properly treated. Once the pressure within the chamber has reached the desired level, i.e. in the range from about 0.01 Torr to about 100 Torr, the metering valve is closed. The vacuum is preferably maintained within the reactor while electromagnetic radiation is being applied for a time sufficient to sterilize the waste gas within the reactor.

Once the metering valve has been closed, application of the vacuum to the chamber is ceased so that a static condition may be developed in the chamber where the pressure throughout the chamber is essentially equal and constant. After the static condition has developed, an amount of starting gas is introduced into the chamber and is allowed to uniformly distribute throughout the chamber. The electromagnetic radiation energy is then applied to the chamber to produce a substantially uniformly distributed plasma within the chamber in a manner similar to the methods previously described. Application of the electromagnetic radiation energy to the starting gas in the chamber is then ceased and the existing gases are exhausted from the chamber. The process of applying a vacuum to the chamber, allowing a static condition to develop, introducing a starting gas into the chamber, and applying electromagnetic radiation energy to the starting gas is repeated until the waste is sufficiently sterilized.

The invention further provides an exemplary system for treating biological waste. The system comprises a sterilization chamber which is adapted to receive biological waste. A treatment reactor is coupled to the chamber such that waste gases from the chamber may be transferred to the reactor. A vacuum pump is coupled to the reactor, and a starting gas source is coupled to the reactor to deliver a starting gas, such as water vapor, to the reactor. An electromagnetic radiation energy generator is coupled to the reactor to deliver electromagnetic radiation energy to the starting gas supplied to the reactor. In this way, a plasma may be produced within the reactor so that waste gases which are transferred from the chamber may be treated within the reactor. Such a system is particularly advantageous because the gases which are exhausted from the sterilization chamber are typically contaminated and need to be treated before their release into the atmosphere. By coupling the treatment reactor to the sterilization chamber, such waste gases may be properly treated before being released.

In one particular aspect, operation of the vacuum pump transfers the waste gases from the chamber to the reactor while also producing a vacuum condition within the chamber which is necessary to treat the waste within the chamber as described in greater detail hereinafter. Preferably, a metering valve is disposed between the reactor and the chamber to control the amount of waste gases supplied to the reactor.

The vacuum pump is preferably also directly coupled to the chamber. A first valve is disposed between the reactor and the vacuum pump, and a second valve is disposed between the chamber and the vacuum pump. In this way, application of a vacuum to the sterilization chamber may be controlled by operation of either the first valve (in combination with the metering valve) or the second valve.

In another aspect, the electromagnetic radiation generator is also coupled to the chamber, and a second starting gas source is coupled to the chamber to allow a plasma to be created in the chamber upon introduction of the starting gas and operation of the electromagnetic radiation energy generator. Conveniently, a controller, such as a computer, may be provided to operate the vacuum, the metering valve, the first and second valves, the electromagnetic radiation generator, and the starting gas sources. In one particular arrangement, the controller is configured to open the metering valve after the electromagnetic radiation energy generator is actuated and a starting gas from the first starting gas source is supplied to the reactor to produce a plasma within the reactor. The controller is further configured to close the metering valve and the first valve after the waste gases within the reactor have been treated. The controller is also configured to then open the second valve and to cyclically actuate the vacuum pump, the second starting gas source, and the electromagnetic radiation generator in a manner similar to that previously described to treat the waste in the chamber. More specifically, the controller is configured to actuate the second gas source to introduce a starting gas into the chamber after the chamber has reached a predetermined pressure and a static condition. The electromagnetic radiation energy generator is then actuated after the introduced gas is uniformly distributed throughout the chamber.

DETAILED DESCRIPTION OF THE SPECIFIC EMBODIMENTS

This invention provides methods and apparatus for sterilizing articles and hazardous biological wastes, and for treating various substrates. When sterilizing articles or hazardous wastes, the invention will employ the use of a gas plasma generated from a gas mixture of oxidizing and reducing agents. In a preferable aspect, the articles are sterilized with a gas plasma that is generated from water vapor. Other gases that may be used include $O_2$, NO, $N_2O$, air, and hydrogen peroxide.

According to the method for sterilizing articles and hazardous biological wastes using a gas plasma that is created from water vapor, at least one article or an amount of waste is introduced into a sterilization chamber. The article can be selected from any of a number of articles, such as surgical instruments, dental instruments, medical products, pharmaceutical products, and the like. Biological waste materials that may be treated include disposable invasive devices, bandages, dressings, gloves, and the like. After the article or waste is within the chamber, a vacuum is applied to the chamber to reduce the pressure within the chamber to a pressure below atmospheric pressure. Preferably, the pressure will be reduced until it is in the range from about 100 mTorr to 10 Torr. When the pressure within the chamber is within the desired range, a water vapor is introduced into the chamber. Conveniently, the water vapor can be introduced into the chamber by a carrier gas. The carrier gas can be any one of a number of gases including such gases as air, argon, hydrogen, nitrogen, oxygen, helium, nitrogen tri-fluoride, nitrous-oxide, and the like, or any mixtures thereof. Preferably, air will be used as the carrier gas. Although such carrier gases can conveniently be used to assist in introducing the water vapor into the chamber, a novel feature of the invention is that water vapor alone can be used to produce the plasma.

Once the water vapor has been introduced into the chamber, electromagnetic radiation energy is applied to the water vapor while the pressure within the chamber is maintained in the desired range. Electromagnetic radiation energy as used herein includes all radio frequency energy and particularly any radio frequency energy having a wavelength in the range from about 5 KHz to 10 GHz, and also includes energy such as microwave, infrared light, visible light, ultraviolet light, laser, X-ray energy and gamma radiation. When the radio frequency energy is supplied, the water molecules are driven into a high energy state, causing the molecules to disassociate into reactive radicals and forming a plasma. The radio frequency energy will preferably be at about 2.45 GHz which has proven to be effective in fractionating the water molecules. The reactive radicals then vaporize and combine with the by-products of spores or other microorganisms on the articles or waste to sterilize the articles or waste. The reactions of the radicals with the spores and other microorganisms produce water vapor, oxygen, hydrogen, and small amounts of carbon dioxide and carbon monoxide. A particular advantage in using water vapor to create the plasma is that when the reactive radicals combine with the spores and other microorganisms on the articles or waste, they are effectively vaporized. In this way, the spores and other microorganisms are physically removed from the articles or waste and converted to gas form which is then exhausted from the chamber. A further advantage in using water vapor to create the plasma is that the exhausted gases, i.e., water vapor, oxygen, hydrogen, and small amounts of carbon dioxide and carbon monoxide, can be safely exhausted into the atmosphere. In still a further advantage, the temperature within the chamber during the sterilization process can be in the range from about 25° C. to about 300° C., with the temperature of the plasma within the chamber being from about 100° C. to about 3000° C. Such temperatures provide for a safe working environment and do not impose additional costs in constructing the sterilization apparatus.

One advantage of this process is that a hazardous biological waste may be sterilized where it is created, thus requiring no special handling, transportation, or storage. Thus, the risk of accidental contamination is low. In this way, the hazardous biological waste may be rendered harmless and then moved through normal channels.

When the hazardous biological waste is within the sterilization chamber and a vacuum is applied to the sterilization chamber, the evacuated gases will typically be contaminated by the hazardous waste. As such, the invention provides for the treatment of the waste gases before they are exhausted into the atmosphere. This is preferably accomplished by transferring the waste gases to a treatment reactor that is coupled to the chamber. Before the waste gases are delivered to the treatment reactor, a vacuum is applied to the reactor and a gas plasma is produced within the treatment reactor. Once the gas plasma has been produced, the waste gases are allowed to enter so that they will be treated. Preferably, the treatment reactor will comprise an long path reactor chamber through which the waste gases will flow. By the time they reach the end of the reactor, the waste gases will have reacted with the plasma to sterilize the waste gases. The waste gases may then be safely exhausted to the atmosphere. Alternatively, discrete amounts of the waste gas may be transferred from the sterilization chamber and into the treatment reactor where a plasma will be produced to sterilize the waste gas. The gas is then exhausted and the process is repeated until all of the waste gas from the sterilization chamber has been treated. Such as process has the effect of a long path reactor chamber that approaches infinity in length, and is useful for treating highly contagious and/or toxic wastes.

Figure 1A:
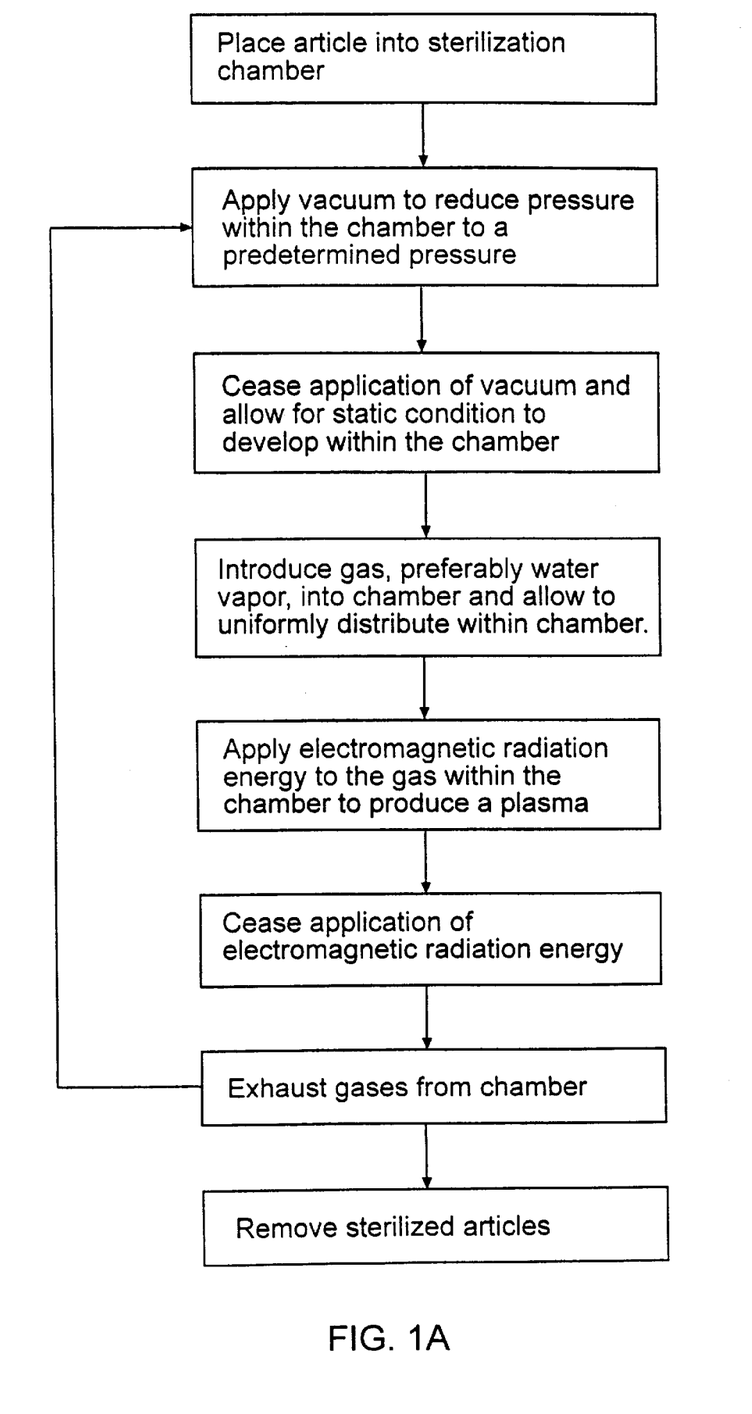
FIG. 1A is a flowchart illustrating an exemplary method for sterilizing articles or biological waste materials using a gas plasma according to the present invention.

An exemplary method for uniformly sterilizing articles, as well as hazardous biological wastes, using a gas plasma is set forth in the flowchart of FIG. 1. According to the method, at least one article (or an amount of biological waste) is placed into a sterilization chamber. The article can be of any size or geometry as long as it can fit within the sterilization chamber. With the article or waste in the chamber, a vacuum is applied to the chamber to reduce the pressure to a predetermined amount. In the case where biological waste is being treated, it may be desirable to treat the gases evacuated from the chamber which may also be contaminated. Such a procedure is described hereinafter with reference to FIGS. 4 and 5.

When the desired pressure is reached, application of the vacuum is ceased and a static condition is allowed to develop in the chamber, i.e., a condition where the pressure remains essentially constant and equal throughout the entire interior of the chamber. Once a static condition has been reached, a discrete amount of a starting gas is introduced into the chamber. Because of the static condition within the chamber, the gas rapidly distributes itself uniformly throughout the entire volume of the chamber as dictated by Boyle's law. This removes gas flow dynamics from the equation.

With the gas equally distributed throughout the entire interior volume of the chamber, electromagnetic radiation, and preferably radio frequency energy, is applied to the gas to produce a plasma. The starting gas can be any one of a number of gases capable of producing reactive radicals, but will preferably include water vapor. The radio frequency energy is applied for a time sufficient to allow the reactive radicals to react with the spores and other microorganisms on the articles. The amount of time the radio frequency energy is applied can be increased as desired to introduce a safety factor. After the plasma has had sufficient time to react, the radio frequency energy is ceased and the resultant gases are exhausted from the chamber.

Because only a discrete amount of gas is introduced at a time into the chamber, the cycle of applying a vacuum to the chamber, allowing a static condition to develop, introducing another amount of gas into the chamber, and applying radio frequency energy can again be repeated as necessary to ensure that the articles within the chamber are sufficiently sterilized.

Figure 1B:
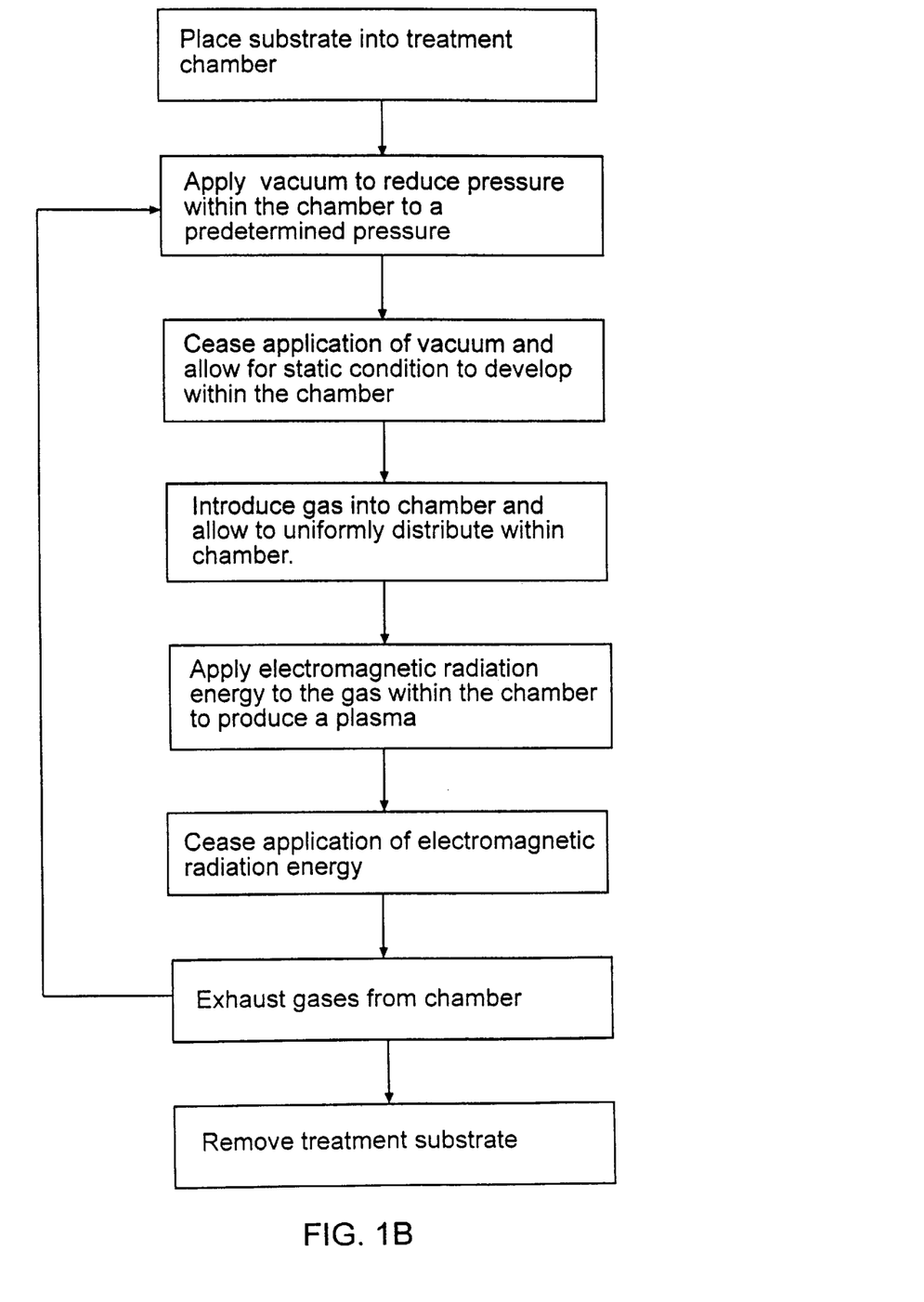
FIG. 1B is a flowchart illustrating an exemplary method for treating substrates using a gas plasma according to the present invention.

The invention further provides an exemplary method for treating various substrates, such as semiconductor substrates, microelectronic substrates, flat panel displays, transducers, and the like. The treatments contemplated by the invention include stripping, cleaning, plasma treating, etching, receiving of a deposition film, and the like. The treatment of the various substrates is similar to the sterilization process previously described and is illustrated in FIG. 1B.

As shown, substrates are treated by placing one or more substrates into a treatment chamber. A vacuum is then applied to the chamber to reduce the pressure to a predetermined amount. At this point, application of the vacuum is ceased and a static condition is allowed to develop within the chamber at the reduced pressure. While at the static condition, a gas or gas mixture is introduced into the chamber and allowed to uniformly distribute itself within the chamber. At this point, electromagnetic radiation energy is applied to the gas within the chamber to produce a plasma. After a specified time, application of the electromagnetic radiation energy is ceased and gasses are exhausted from the chamber. To sufficiently treat the substrate, the cycle may be repeated as many times as needed.

One particular advantage of such a method is that the gas is injected into a static reaction chamber volume. Under such conditions, the pressure is equalized and the concentration of gasses is uniform throughout the entire volume of the chamber. By providing a uniform gas distribution, a uniform plasma treatment may be provided by applying electromagnetic radiation energy to the gas.

Application of the electromagnetic radiation drives the gas molecules into a high energy state causing them to fractionate to create reactive radicals. The reactive gasses are then used to treat the substrates.

Such a method for treating the substrates is further advantageous in that relatively large substrates may be uniformly treated. Since no gas flow dynamics exist within the chamber, every point of the substrate within the chamber will experience approximately the same plasma treatment. In this manner, the size of substrate is limited only by the size of the chamber. For example, substrates that are 1 m by 1 m or greater may be uniformly treated. Similarly, the batch size is limited only by the size of the chamber. In this manner, multiple substrates may be treated simultaneously, with each substrate being uniformly treated. In a further advantage, since the plasma density is uniform in the reaction chamber, high yields are possible, therefore making the treatment of substrates extremely efficient.

The types of gasses introduced into the chamber will vary depending upon the particular treatment. For example, various substrates may be subjected to a reactive ion etching process using $CF_4$, $CHF_3$, $NF_3$, $SF_6$, $CCl_2F_2$, $CCl_4$, $SiCl_4$, $BCl_3$, HCl, HBr, Clr, $CF_8$, and the like. These gases may be used individually or in combination, and with or without the presence of $O_2$, NO, $N_2O$, $H_2O$ or $O_3$. Such gasses areparticularly useful when etching oxides, nitrides, silicons, polysilicons, polyamide, Ta, Ti, W, and the like. The process may also be employed to etch various metals, such as aluminum, nickel, gold, and the like. Exemplary gasses for etching such metals include $CL_2$, $CCL_4$, $SiCL_4$, $BCL_3$, and other chlorine-bearing gasses including $CCl_2F_2$.

Exemplary gasses for photoresist stripping processes for wafers or other substrates include water vapor, $O_2$, NO, $N_2O$, air, $H_2$, $N_2$, Hl, Ar, and the like, alone or in combination. Exemplary gasses for depositing a film include $SiH_4$, $NH_3$, $N_2O$, NO, Ar, $WF_6$ and/or other organic compounds.

When treating the various substrates, the reaction chamber will preferably be evacuated to a pressure in the range from about 1 mTorr to about 10 Torr. Preferable ranges for the applied electromagnetic radiation energy will be in the range from about 5 KHz to about 10 GHz.

Figure 2:
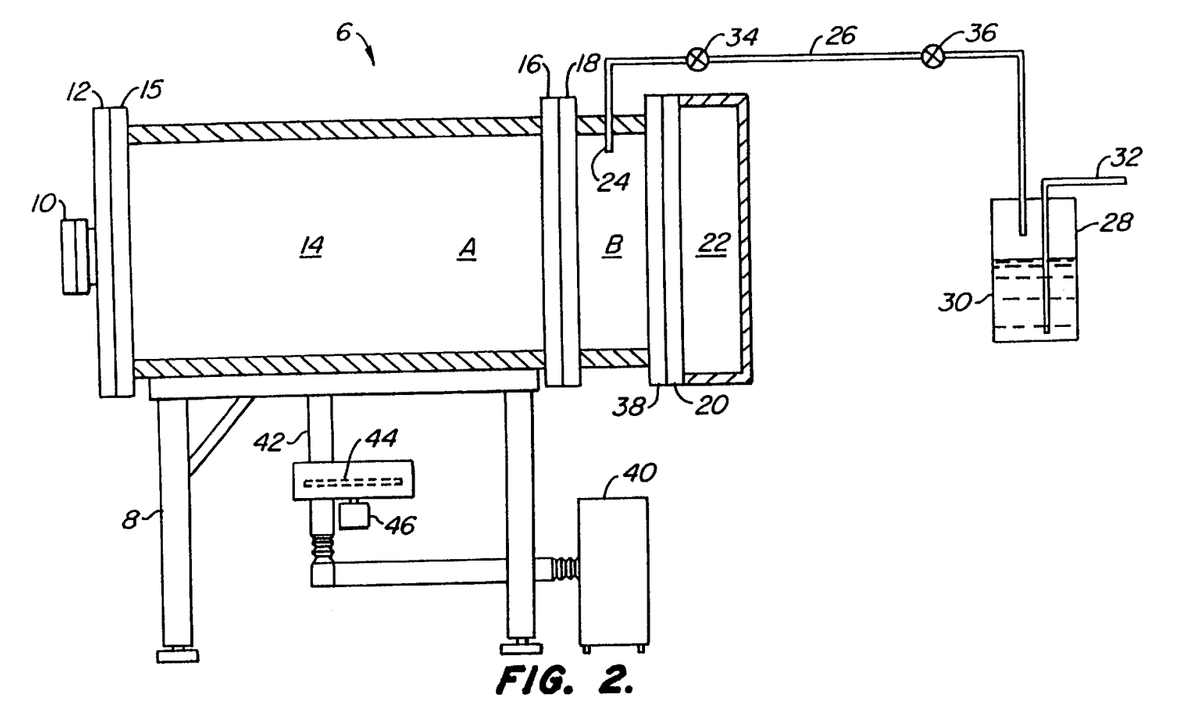
FIG. 2 illustrates a partially cut-away side view of a sterilization or treatment apparatus according to the present invention.

Referring to FIG. 2, an exemplary embodiment of an apparatus 6 that may be employed to sterilize articles or hazardous waste as set forth in FIG. 1A or to treat various substrates as set forth in FIG. 1B will be described. The apparatus 6 is conveniently placed on a table 8 for easier access. The apparatus 6 includes a view port 10 within a door 12. The door 12 is connected to a reaction chamber 14 via a flange 15. Visual access to the reaction chamber 14 is obtained through the view port 10, while physical access is gained by opening the door 12. Preferably, the door 12 will be hingedly connected to the flange 15. The door 12, the flange 15, and the chamber 14 will preferably all be constructed of stainless steel. Use of stainless steel for these components is advantageous because the stainless steel has a lower sputter yield (i.e., the physical deposition of material on substrates) than would aluminum or aluminum oxide, causing damage and contamination to the articles being sterilized or to the substrates.

Attached to an opposite end of the reaction chamber 14 is another stainless steel flange 38. The flange 38 is used to attach a material transparent to electromagnetic radiation energy, such as a glass or quartz plate seal 20 through which electromagnetic radiation energy is directed.

To inject gas into the reaction chamber 14, a gas injection port 24 is provided. Gas is supplied to the injection port 24 through a gas line 26. In turn, the gas line 26 is in communication with a gas source 28. The gas source 28 can be configured to provide any one of a variety of gases, and will preferably be configured to provide water vapor as the gas. To provide the water vapor, the gas source 28 includes a container 30 having an amount of water $H_2O$. Placed in the water is a carrier gas delivery tube 32 for bubbling a carrier gas through the water. In this way, as the carrier gas is bubbled through the water, water vapor is produced which can be delivered to the reaction chamber 14 through the gas line 26. A gas injection valve 34 is provided for controlling injection of the gas into the reaction chamber 14. A gas metering valve 36 is provided to meter the amount of gas travelling through the gas line 26.

Although shown with only a single gas injection port 24, the apparatus 6 can alternatively be provided with a plurality of gas injection ports disposed throughout the reaction chamber 14. In such a configuration, a header can be provided to distribute the gas to the various gas injection ports around the reaction chamber 14.

A electromagnetic radiation energy source 22 is provided for supplying electromagnetic radiation energy into the chamber at a wavelength in the range from about 5 KHz to 10 GHz. Preferably, the electromagnetic radiation energy supplied by the generator source 22 will be at about 2.45 GHz for the sterilization process. Such a wavelength is the same wavelength produced by most commercially available microwave sources. Conveniently, the generator source 22 can be constructed from a commercially available microwave source. The electromagnetic radiation energy is directed through the plate seal 20 and into the reaction chamber 14. As previously described, the plate seal 20 is constructed of a material transparent to electromagnetic radiation energy, and is preferably constructed of a glass or a quartz plate. The stainless steel flange 38 is provided to attach to the generator source 22 to the reaction chamber 14.

The gas injected into the reaction chamber 14 is allowed to equally distribute itself throughout the entire interior volume of the reaction chamber 14. This is accomplished by sealing the chamber 14 after the gas is injected. When the gas is within the reaction chamber 14, the electromagnetic radiation generator source 22 can be actuated to direct energy through the plate seal 20 and into the reaction chamber 14. In this way, a plasma is produced when the gas is energized by the electromagnetic radiation energy.

In some instances, it may be desirable to provide a diffuser plate 18. The diffuser plate 18 is held by a flange 16 and divides the reaction chamber 14 into two separate volumes. The volume adjacent the door 12 (volume A) is for holding the articles and the volume adjacent the generator source 22 (volume B) is for receiving the injected gas. The diffuser plate 18 contains at least one through hole so that the two volumes A, B can communicate. More than one through hole can be included for multiple point injection of the gas. As gas is injected into volume B adjacent the electromagnetic radiation generator source 22, this volume is immediately filled with gas. Volume A is also almost immediately filled with the gas through the through hole. The rate at which volume A is filled can be varied depending on the pressure difference between the volumes A, B and the size and quantity of through holes.

At this point, it is possible to produce a plasma in volume B, but not in volume A. As described hereinafter, plasma can alternatively be produced in both volume A and B in any proportion so that the articles in volume A can be exposed only to the reactive gases, or to any combination of reactive gases and ionic bombardment. To produce the plasma only in volume B, a metallic cover is placed adjacent the plate 18 (or substituted for plate 18) to prevent radiation energy from entering volume A when the electromagnetic radiation generator 22 is actuated to produce a plasma in volume B. In this way, the articles in volume A receive no ionic bombardment and are only exposed to the previously diffused reactive gases in volume A. This procedure is particularly beneficial when sterilizing sensitive articles such as cameras, microscopes, optics, implantable sensors, lenses, and the like.

To sterilize without ionic bombardment over a broader range of parameters, a second metal gas diffusion plate with one or more through holes can be rotatably received relative to the first plate. As the second plate is rotated relative to the first plate, the through holes come in and out of alignment allowing for varying degrees of gas diffusion into volume A.

The electromagnetic radiation generator source 22 can be actuated at different times relative to the injection of the gas into the volume B to vary the amount of plasma diffused into the volume A. If the electromagnetic radiation energy is actuated just as the gas is injected into the volume B, then a plasma will be created that can then be diffused into the volume A. If the generator source 22 is actuated well after the gas has diffused into the volume A, then virtually no plasma will be diffused into the volume A.

In some circumstances, particularly when using low frequency electromagnetic radiation energy, it may be difficult to couple the electromagnetic radiation energy through the plate seal 20. In such a case, the electromagnetic radiation energy can be inductively or capacity coupled through the glass or quartz plate 20 into the reaction chamber. To capacity couple the energy source, an electrode can be employed and placed either inside or outside the reaction chamber 14. Use of the electrode inside the chamber 14 is useful when using electromagnetic radiation energy having a frequency of 10 MHz or less. Use of the electrodes outside the chamber is useful when using electromagnetic radiation energy having frequencies in the range from 10 MHz to 900 MHz. To inductively couple, a metal tube or bar, preferably having a diameter in the range from 3/16" to 1/4" is arranged on the outside surface of the plate 20. Energy is supplied through the wire at a frequency in the range of about 10 MHz to 900 MHz and is coupled through the plate 20 to produce the plasma.

The reaction chamber 14 can be constructed of any geometry, but will preferably be orthogonal or cylindrical in geometry. An orthogonal geometry is advantageous when using trays to carry the articles to be sterilized. Use of trays allows for easy arrangement of the articles within the chamber 14.

To reduce the pressure within the reaction chamber 14 prior to injection of the gas, a vacuum pump 40 is provided. The vacuum pump 40 can be any pump capable of reducing pressures within the reaction chamber 14 down to a pressure of about 10 mTorr. An exemplary vacuum pump 40 is one such as the Alcatel 1220, commercially available from Alcatel. The vacuum pump 40 also serves to exhaust gases from the reaction chamber 14 after sterilization or other treatment has occurred. The vacuum pump 40 communicates with the reaction chamber 14 via an exhaust port 42.

As previously described in the methods of the invention, it is desirable to provide a uniformly distributed plasma within the chamber 14 regardless of the geometry of the reaction chamber 14 or the articles or substrates themselves. To provide a uniform plasma treatment, a static condition is created within the chamber 14 by ceasing the pumping. A discrete amount of gas, i.e., a known volume, can be injected into the reaction chamber 14 through the port 24 which is then closed. The gas is then allowed to equally distribute itself throughout the entire interior volume of the reaction chamber 14. Electromagnetic radiation energy from the generator source 22 is directed into the chamber 14 to create a uniform plasma, thereby allowing for uniform sterilization or treatment of the articles or substrates regardless of their size or geometry. The sterilizing and/or treatment procedures are accomplished with one or more sterilization cycles.

In order to insure sufficient sterilization or treatment when only a discrete amount of gas is introduced, the apparatus 6 includes a controller for controlling a repeating sterilization cycle. The controller separately and repeatedly actuates the vacuum, the gas injection, the electromagnetic radiation energy, and the exhausting of spent gases. In this way, the articles or substrates within the sterilization or treatment chamber are continually subjected to a series of uniformly distributed gas plasma.

Figure 3:
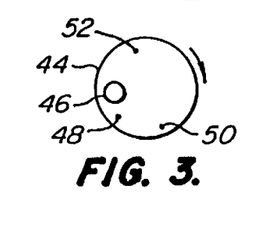
FIG. 3 illustrates a top view of a rotating chopper valve for controlling the sterilization or treatment cycle of the apparatus of FIG. 2.

The controller can be any controller capable of separately actuating the vacuum pump 40, the gas injection valve 34, actuation of the generator source 22, and the exhaustion of gases through the exhaust port 42 in a systematic and controlled manner. An exemplary controller for controlling a sterilization or treatment cycle as just described is illustrated in FIGS. 2 and 3. The controller includes a rotating chopper valve 44 that is rotated by a chopper valve drive motor 46. A top view of the chopper valve 44 is shown in FIG. 3. The chopper valve 44 includes an orifice 46 that is alignable with the exhaust port 42. As the chopper valve 44 rotates, the orifice 46 passes in and out of alignment with exhaust port 42. The vacuum pump 40 is continuously actuated so that a vacuum will be applied to the reaction chamber 14 as the orifice 46 becomes aligned with the exhaust port 42. Disposed on the chopper valve 44 are a series of indicators which can be sensed by a sensor, such as an optical sensor (not shown), and used to actuate the gas injection valve 34 and the generator source 22. A gas injection indicator 48 is provided for actuating the valve 34 to inject a gas through the gas injection port 24. Spaced-apart from the gas injection indicator 48 is a electromagnetic radiation "on" indicator 50. As the electromagnetic radiation "on" indicator passes the sensor, a signal is sent to actuate the electromagnetic radiation generator source 22. The electromagnetic radiation energy source 22 remains actuated until the sensor senses a electromagnetic radiation "off" indicator 52.

The sensor will preferably be connected to a microprocessor or other controller for sending signals to actuate the generator source 22 and the gas injection valve 34 so that gas can be injected and electromagnetic radiation energy can be applied at the appropriate times.

In this way, the chopper valve 44 acts as an event timer which controls a sterilization or treatment cycle capable of producing a series of uniformly distributed plasma treatments within the reaction chamber 14, regardless of its size or geometry. As the chopper valve 44 rotates, the orifice 46 comes into alignment with the exhaust port 42 thereby creating a vacuum within the chamber 14. As the orifice 46 passes out of alignment, the vacuum is stopped and a static condition is allowed to develop within the chamber 14. At this point, the sensor senses the gas injector indicator 48 which sends a signal to open the valve 34 and to inject gas into the reaction chamber 14 through the gas injection port 24. Because of the static condition within the chamber 14, the gas uniformly distributes itself throughout the reaction chamber 14. The sensor then senses the electromagnetic radiation "on" indicator and a signal is sent to the electromagnetic radiation generator source 22 to apply electromagnetic radiation energy to the gas and to produce a uniformly distributed gas plasma which reacts with the microorganisms on the articles or otherwise treats the substrates. The sensor then senses the electromagnetic radiation "off" indicator 52 and sends a signal to cease application of the electromagnetic radiation energy. The orifice 46 then comes back into alignment with the exhaust port 42 to exhaust the spent gases and to again create a vacuum within the chamber 14. The cycle is then repeated as often as necessary until the sterilization or treatment procedure is complete. The repetition rate of the cycle is a function of the rotational speed of the chopper valve 44, and the duration of any given event in the cycle is a function of the placement of the indicators 48–52 on the chopper valve 44. Preferably, the cycle will be repeatable up to about 100 cycles per minute. Although the controller for controlling the sterilization or treatment cycle of the apparatus 6 has been described in connection with the chopper valve 44, any controller capable of separately actuating the events in the cycle can be employed. For example, a personal computer could be configured to sequentially actuate the pump 44, the injection valve 34, and the generator source 22.

The invention further provides a method and apparatus for sterilizing articles that are prepackaged in a container. When articles are manufactured, it is desirable to deliver them to the end user in a sterile protective package. This may require sterilizing the articles and then packaging them in a sterile environment. This invention eliminates such a procedure by sterilizing the articles while within their packaging materials. To sterilize the articles in this manner, the invention employs a packaging container for prepackaging the articles. The container is constructed of a material transparent to electromagnetic radiation frequency energy, such as plastic. The articles are placed in the container, and before the container is sealed the container is pumped to a vacuum of about 1 mTorr to 100 mTorr. The container is then back-filled with water vapor to a pressure of about 100 mTorr to 100 Torr. To back-fill the water vapor, a carrier gas is employed. The carrier gas is preferably air, but other gases can be employed such as argon, hydrogen, nitrogen, oxygen, helium, nitrogen tri-fluoride, nitrous oxide or mixtures thereof.

The prepackaged articles are then sterilized by placing the container in close proximity to an electromagnetic radiation source. The energy source is activated for a predetermined time to form a highly energetic water vapor. The electromagnetic radiation energy is then ceased for a predetermined time so that a static condition can develop within the container. This allows the pressure to become equalized and the concentration of the gases to become uniform throughout the volume of the container. The electromagnetic radiation energy is then reactivated to produce a uniformly distributed plasma. The energy source remains on for a predetermined time and the cycle may be repeated as many times as needed to complete the sterilization process. During the process the reactive radicals in the plasma vaporize and combine with the by-products of spores or other microorganisms on the articles. This produces water vapor, oxygen, nitrogen, and small amounts of carbon dioxide and carbon monoxide which all remain in the package until opened. However, the combination of these gases is inert and can be safely exhausted into the atmosphere when the containers are opened. In this way, the articles in the container remain sterilized until they are removed for use.

Figure 4:
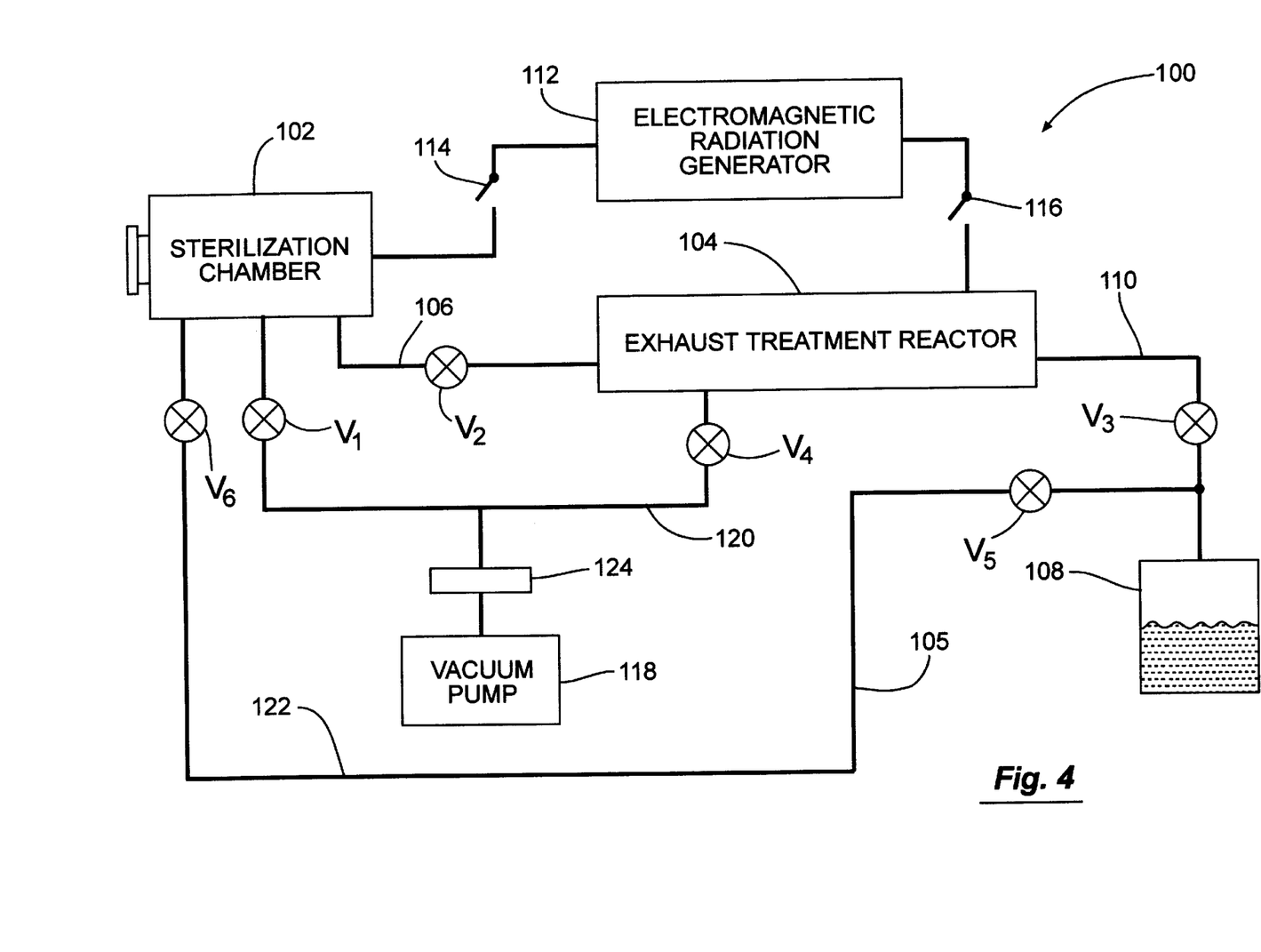
FIG. 4 is a schematic diagram of an exemplary system for treating biological waste materials according to the invention.

Referring now to FIG. 4, an exemplary system 100 for treating hazardous biological waste materials will be described. System 100 comprises a sterilization chamber 102 which may be constructed to be essentially identical to sterilization chamber 14 of FIG. 2. Chamber 102 is coupled to an exhaust treatment reactor 104 by a line 106. Disposed in line 106 is a metering valve $V_2$ to control the flow of waste gases from chamber 102 to reactor 104. Reactor 104 is preferably a long path reactor, typically having a path length of at least five meters, to allow waste gases flowing through reactor 104 to be sufficiently treated.

System 100 further includes a gas source 108 to provide a starting gas, i.e. a gas, such as water vapor, which will produce a gas plasma when subjected to electromagnetic radiation energy, to reactor 104 via a line 110. A valve $V_3$ is disposed in line 110 to control introduction of gases from gas source 108 to reactor 104. Gas source 108 may include any one of a variety of gases suitable for producing a gas plasma within exhaust treatment reactor 104 as previously described. Gas source 108 is also coupled to sterilization chamber 102 by a line 105 to provide starting gases to chamber 102. Line 105 includes valves $V_5$ and $V_6$ which operate in a similar manner to valves 36 and 34, respectively, of the system of FIG. 2.

An electromagnetic radiation generator 112 is provided to supply electromagnetic radiation energy to reactor 104 and chamber 102 in a manner similar to that previously described in connection with FIG. 2. A pair of switches 114 and 116 are provided to selectively couple chamber 102 and reactor 104, respectively, to generator 112. Electromagnetic radiation generator 112 may be constructed to be similar to electromagnetic radiation energy source 22 of FIG. 2.

System 100 includes a vacuum pump 118 which is coupled to reactor 104 via a line 120, and to chamber 102 via a line 122. Valves $V_4$ and $V_1$ are provided in lines 120 and 122, respectively, to control application of a vacuum to either reactor 104 or chamber 102. In communication with vacuum pump 118 is a chopper valve system 124 which is similar to chopper valve 44 and associated equipment of FIGS. 2 and 3. Although not shown, system 100 includes a controller, such as a Pentium-type personal computer, to control interaction of the various components of system 100 as described in greater detail hereinafter with reference to FIGS. 5 and 6.

System 100 may be operated in one of two ways to sterilize waste gases from chamber 102. According to one method, the waste gases are continuously removed from chamber 102 and treated as they flow through reactor 104. Alternatively, discrete amounts of the waste gas may be removed from chamber 102 and then treated in reactor 104 using a cyclical process.

Figure 5:
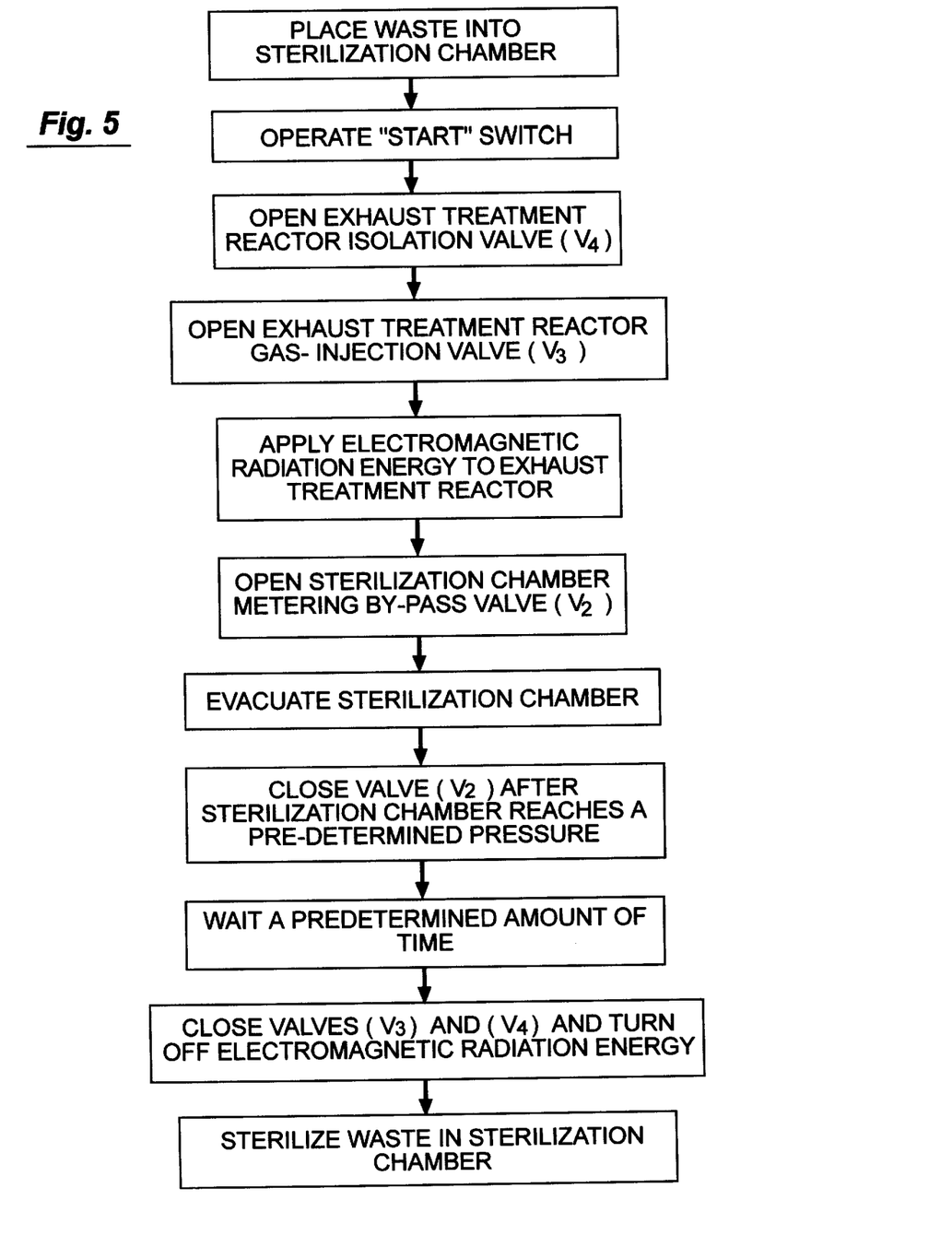
FIG. 5 is a flow chart illustrating an exemplary method for operating the system of FIG. 4 to treat biological waste materials according to the invention.

Referring now to FIG. 5, operation of system 100 to treat biological waste will be described according to one method. Initially, system 100 is in an automatic mode where the controller is operating to control the various elements of system 100. Initially, each of valves $V_1$–$V_4$ are closed and sterilization chamber 102 is at atmospheric pressure. A biological hazardous waste material to be sterilized is then placed into chamber 102. A start button on the controller is then actuated to begin operation of vacuum pump 118. Valve $V_4$ is opened to allow a vacuum to be produced within reactor 104, and valve $V_3$ is opened to supply gas from gas source 108 into reactor 104. Electromagnetic radiation energy generator 112 is actuated and switch 116 is closed to supply electromagnetic radiation energy to reactor 104. In turn, a plasma gas is created within reactor 104 in a manner similar to that previously described in other embodiments.

Metering valve $V_2$ is then opened, with the vacuum within the reactor 104 causing gases within chamber 102 to be transferred into reactor 104. At the same time, a vacuum condition is produced within chamber 102 which will be necessary to create a plasma gas within chamber 102 as described in greater detail hereinafter. The gases transferred from chamber 102 to reactor 104 are typically contaminated since they were previously surrounding the waste material within chamber 102. As the waste gases pass through treatment reactor 104, they interact with the gas plasma to sterilize the waste gases. Preferably, treatment reactor 104 will have a sufficient length so that as the waste gases exit reactor 104 they will be sterilized before being exhausted into the atmosphere. Metering valve $V_2$ assists in this process to assure that appropriate levels of waste gases are supplied to treatment reactor 104.

Once sterilization chamber 102 has reached a predetermined pressure (which is preferably within the same pressure range as that employed to operate sterilization chamber 14 of FIG. 2 as previously described), metering valve $V_2$ is closed by the controller. Preferably, the sterilization process within treatment reactor 104 will then continue until all residual waste gases from chamber 102 have been treated and exhausted into the atmosphere.

After valve $V_2$ has closed and a sufficient time has passed to insure the sterilization of the waste gases, the controller opens switch 116 and closes valves $V_3$ and $V_4$. Sterilization of the biological waste previously placed in sterilization chamber 102 then begins. The sterilization procedure preferably proceeds in a manner essentially identical to that previously described with reference to FIG. 1A. In particular, a static condition is preferably allowed to develop within chamber 102. A gas is then introduced into chamber 102 and allowed to uniformly distribute within the chamber. Switch 114 is then closed to allow radiation energy to be supplied to the gas within chamber 102 to produce a plasma. Application of electromagnetic radiation energy is then ceased. The process is then repeated as many times as is needed in order to sufficiently sterilize the waste within chamber 102.

During the cycle, valve $V_1$ is opened and chopper valve system 124 is employed to regulate the application of vacuum to chamber 102 and to exhaust the gases after the plasma has been produced in a manner similar to that previously described. Once the waste is sufficiently sterilized, it may be removed from chamber 102 and safely discarded.

Figure 6:
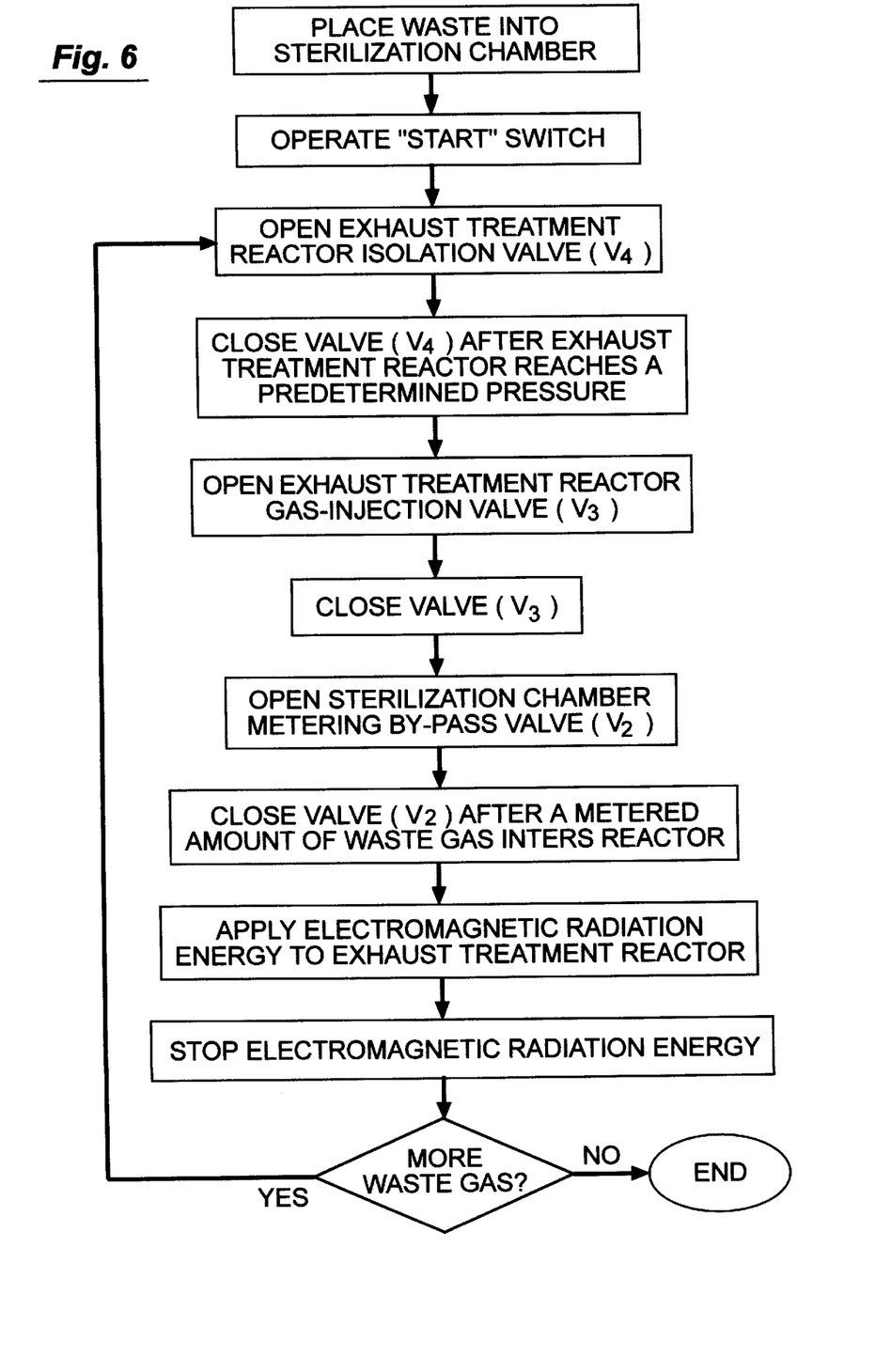
FIG. 6 is a flow chart illustrating an alternative method for operating the system of FIG. 4 to treat biological waste materials according to the invention.

Referring to FIG. 6, an alternative method for operating system 100 will be described. Initially the waste is placed into chamber 102 and the start button is turned on similar to the method of FIG. 5. Valve $V_4$ is then opened to apply a vacuum to reactor 104. Valve $V_4$ is closed after reactor 104 has reacted a predetermined pressure. Valve $V_3$ is then opened to supply gas from source 108 to reactor 104. Valve $V_3$ is then closed and valve $V_2$ is opened to inject a discrete, metered amount of waste gas from chamber 102 into reactor 104. After the metered amount has been injected, valve $V_2$ is closed and the waste gas is allowed to uniformly distribute itself within reactor 104. Electromagnetic radiation generator 112 is then actuated and switch 116 is closed to supply electromagnetic radiation energy to reactor 104. This creates a plasma gas to treat the waste gas. Once treated, the gas is exhausted, valve $V_4$ is reopened and the process is repeated until all of the waste gas from chamber 102 has been treated. The waste within chamber 102 may then be sterilized as previously described.

Although the foregoing invention has been described in detail by way of illustration and example, for purposes of clarity of understanding, it will be obvious that certain changes and modifications may be practiced within the scope of the appended claims.

What is claimed is:

1. A method for treating a hazardous biological waste, comprising:

(a) placing the waste into a chamber;

(b) applying a vacuum to a reactor which is coupled to the chamber;

(c) introducing an amount of a starting gas into the reactor;

(d) applying electromagnetic radiation energy to the starting gas in the reactor to produce a plasma within the reactor;

(e) transferring at least some of a contaminated waste gas within the chamber to the reactor while the radiation energy is being applied to the starting gas within the reactor, wherein the transfer of the contaminated gas reduces the pressure within the chamber;

(f) introducing an amount of a starting gas into the chamber when the pressure within the chamber reaches a desired level; and (g) applying electromagnetic radiation energy to the starting gas in the chamber to produce a plasma within the chamber.

2. A method as in claim 1, further comprising initiating application of the vacuum to the reactor and application of the electromagnetic radiation energy to the starting gas in the reactor prior to transferring the waste gas to the reactor.

3. A method as in claim 1, further comprising transferring the waste gas from the chamber to the reactor through a metering valve by application of the vacuum to the reactor when the metering valve is open.

4. A method as in claim 3, further comprising closing the metering valve when a desired pressure is reached within the chamber.

5. A method as in claim 4, further comprising continuing application of the vacuum to the reactor and the electromagnetic radiation energy to the starting gas in the reactor for a predetermined amount of time after the metering valve is closed.

6. A method as in claim 4, wherein closing of the metering valve ceases application of the vacuum to the chamber and allows a static condition to develop in the chamber where the pressure throughout the chamber is essentially equal and constant.

7. A method as in claim 6, wherein, after the static condition has developed, the amount of starting gas is introduced into the chamber and is allowed to uniformly distribute throughout the chamber.

8. A method as in claim 7, wherein the electromagnetic radiation energy is applied to the chamber after the starting gas has become uniformly distributed within the chamber to produce a substantially uniformly distributed plasma within the chamber.

9. A method as in claim 8, further comprising:

(h) ceasing application of the electromagnetic radiation energy to the starting gas in the chamber;

(i) exhausting gases from the chamber;

(j) applying a vacuum to the chamber; and (k) repeating the steps (f) and (g).

10. A method as in claim 1, wherein the starting gas is selected from the group of gases consisting of water vapor, $O_2$, NO, $N_2O$, air, and hydrogen peroxide.

11. A method as in claim 10, wherein the water vapor is introduced into the chamber with a carrier gas.

12. A method as in claim 11, wherein the carrier gas is selected from the group consisting of air, argon, oxygen, nitrogen, helium, nitrous oxide and nitrogen tri-fluoride.

13. A method as in claim 1, wherein the electromagnetic radiation energy is in the range from about 5 KHz to 10 GHz.

14. A method as in claim 13, wherein the electromagnetic radiation energy is about 2.45 GHz.

15. A method as in claim 1, wherein the pressure within the chamber when the starting gas is introduced is in the range from about 0.01 Torr to 100 Torr, and wherein the temperature within the chamber is in the range from about 25° C. to 1000° C.

16. A system for treating biological waste, comprising:

a sterilization chamber which is adapted to receive biological waste;

a treatment reactor coupled to the chamber such that waste gases from the chamber may be transferred to the reactor;

a vacuum pump coupled to the reactor;

a starting gas source coupled to the reactor to deliver starting gas to the reactor; and an electromagnetic radiation energy generator coupled to the reactor to deliver electromagnetic radiation energy to the starting gas supplied to the reactor to produce a plasma within the reactor so that waste gasses which are transferred from the chamber are treated within the reactor.

17. A system as in claim 16, further comprising a metering valve disposed between the chamber and the reactor, wherein the metering valve is operable to place the reactor in communication with the chamber and to allow waste gasses within the chamber to be transferred to the reactor upon operation of the vacuum pump.

18. A system as in claim 17, wherein the vacuum pump is further coupled to the chamber, and further comprising a first valve disposed between the reactor and the vacuum pump and a second valve disposed between the chamber and the vacuum pump.

19. A system as in claim 18, wherein the electromagnetic radiation energy generator is further coupled to the chamber, and further comprising a second starting gas source coupled to the chamber such that a plasma gas may be created in the chamber upon introduction of the starting gas and operation of the electromagnetic radiation energy generator.

20. A system as in claim 19, further comprising a controller which is configured to operate the vacuum, the metering valve, the first valve, the electromagnetic radiation energy generator, and the first starting gas source.

21. A system as in claim 20, wherein the controller is configured to open the metering valve after the electromagnetic radiation energy generator is actuated and starting gas from the first starting gas source is supplied to the reactor to produce a plasma within the reactor.

22. A system as in claim 21, wherein the controller is further configured to close the metering valve and the first valve after waste gasses within the reactor have been treated, and wherein the controller is further configured to open the second valve, and to cyclically actuate the vacuum pump, the second starting gas source, and the electromagnetic radiation energy generator to treat the waste in the chamber.

23. A system as in claim 22, wherein the controller is configured to actuate the vacuum pump, the second starting gas source, and the electromagnetic radiation energy generator at separate times.

24. A system as in claim 23, wherein the controller actuates the second gas source to introduce starting gas into the chamber after the chamber has reached a predetermined pressure and a static condition.

25. A system as in claim 24, wherein the controller actuates the electromagnetic radiation energy generator after the introduced gas has uniformly distributed throughout the chamber.

26. A system as in claim 25, wherein the vacuum pump is connected to the sterilization chamber by a tube, and wherein the controller includes a rotatable disk having an orifice alignable with the tube upon rotation of the disk, whereby alignment of the orifice and the tube creates a vacuum within the chamber.

27. A system as in claim 26, further comprising a sensor to sense the degree of rotation of the disk and to send a signal to actuate the second gas source or the electromagnetic radiation energy generator depending on the degree of rotation of the disk.

28. A method for treating a hazardous biological waste, comprising:

(a) placing the waste into a chamber;

(b) applying a vacuum to a reactor which is coupled to the chamber;

(c) introducing an amount of starting gas into the reactor;

(d) applying electromagnetic radiation energy to the starting gas in the reactor to produce a plasma within the reactor;

(e) transferring at least some of a contaminated waste gas within the chamber to the reactor while the radiation energy is being applied to the starting gas within the reactor.

29. A method as in claim 28, further comprising:

(f) applying a vacuum to the chamber;

(g) introducing an amount of starting gas into the chamber when the pressure within the chamber reaches a desired level; and (h) applying electromagnetic radiation energy to the starting gas in the chamber to produce a plasma within the chamber.

30. A method as in claim 28, further comprising exhausting the treated waste gas from the reactor.

31. A method for treating a hazardous biological waste, comprising:

(a) placing the waste into a chamber;

(b) transferring at least some of a contaminated waste gas from the chamber into a reactor;

(c) producing a plasma within the reactor to treat the waste gas; and (d) producing a plasma within the chamber to treat the waste.

32. A method as in claim 31, further comprising repeating steps (b) and (c) until substantially all of the waste gas has been sterilized before performing step (d).

33. A method for treating a hazardous biological waste, comprising:

(a) placing the waste into a chamber;

(b) applying a vacuum to the chamber;

(c) ceasing application of the vacuum and allowing a static condition to develop in the chamber where the pressure throughout the chamber is essentially equal and constant;

(d) after the static condition has developed, introducing an amount of gas into the chamber and allowing the gas to uniformly distribute throughout the chamber; and (e) applying electromagnetic radiation energy to the chamber after the gas has become uniformly distributed within the chamber to produce a substantially uniformly distributed plasma within the chamber.

34. The method of claim 33, further comprising:

(f) ceasing application of the electromagnetic radiation energy;

(g) exhausting gases from the chamber; and (h) repeating the steps (b) through (g).

* * * * *